(12) United States Patent
Jagdharry et al.

(10) Patent No.: US 11,752,080 B1
(45) Date of Patent: Sep. 12, 2023

(54) BINDER FOR USE IN POWDERY COSMETIC COMPOSITIONS

(71) Applicant: ELC Management LLC, Melville, NY (US)

(72) Inventors: Lalita Jagdharry, Oshawa (CA); Hoda Othman, New Market (CA); Mayara Gusmao, Markham (CA); David Singh, Scarborough (CA)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 17/819,350

(22) Filed: Aug. 12, 2022

(51) Int. Cl.
*A61K 8/37* (2006.01)
*A61K 8/02* (2006.01)
*A61K 8/92* (2006.01)
*A61Q 1/10* (2006.01)
*A61K 8/67* (2006.01)

(52) U.S. Cl.
CPC ............... *A61K 8/37* (2013.01); *A61K 8/022* (2013.01); *A61K 8/375* (2013.01); *A61K 8/678* (2013.01); *A61K 8/922* (2013.01); *A61Q 1/10* (2013.01); *A61K 2800/412* (2013.01); *A61K 2800/436* (2013.01); *A61K 2800/524* (2013.01)

(58) Field of Classification Search
None
See application file for complete search history.

(56) References Cited

U.S. PATENT DOCUMENTS

2012/0276027 A1* 11/2012 Kessler ................ A61Q 1/10
424/59

FOREIGN PATENT DOCUMENTS

EP 1033126 B1 6/2004
WO WO-2018/004148 A1 1/2018

* cited by examiner

*Primary Examiner* — Nannette Holloman
(74) *Attorney, Agent, or Firm* — Peter Giancana

(57) ABSTRACT

Powdery cosmetic compositions comprise a particulate phase and a binder sub- composition. The binder sub-composition consists of a viscous emollient, a non-viscous emollient, a triglyceride ester fatty acid, and one or more specific waxes. The binder sub-composition is particularly suited for use in stabilizing pearlescent and metallic pigments. The compositions are stable, have a creamy texture, and are suitable for long-wear, while providing true color, excellent color payoff and skin conditioning.

8 Claims, No Drawings

BINDER FOR USE IN POWDERY COSMETIC COMPOSITIONS

FIELD OF THE INVENTION

The present disclosure generally relates to powdery makeup compositions for the skin and hair. More particularly, the present disclosure relates to powdery eye makeup compositions that comprise metallic, pearlescent or other color effect pigments.

BACKGROUND OF THE INVENTION

In the field of cosmetics, pearlescent pigments create interference effects that depend on the angles of illumination and observation. For example, pearlescent pigments may produce a deep gloss and sheen when applied to the skin surface. The look conferred by pearlescent pigments is considered aesthetically pleasing, glamorous, and sensual. Typical pearlescent pigments are plate-like particles that consist of mica coated with titanium dioxide and/or iron oxides. The thickness of the coating varies, which gives rise to a range of refractive indices and an assortment of visual effects. Particle size will also affect the feel of the cosmetic when applied to the skin. Roughly speaking, pearlescent pigments in the range of 1-15 μm confer a velvety feel and a matte shimmer. As pigment size increases slightly (5-25 μm) the feel becomes more silky and the visual effect more satin. As pigment size is further increased (about 50 μm), a sparkly appearance develops. This sparkle effect is increasingly pronounced as pigment size increases at least to about 500 μm.

Cosmetic metallic pigments are very thin platelet-shaped particles typically made out of borosilicates, synthetic fluorphlogopite and mica. Light is reflected from these pigments, but the amount of light perceived by the eye is heavily dependent on the viewing angle. Metallic pigments offer sparkle and gloss. The exact behavior depends on the size and shape of the metallic particles.

A pressed powder is one type of delivery system for metallic and pearlescent pigments. Pressed power compositions usually include a particulate phase and a binder phase. The particulate phase may comprises various dry powders and pigments. In general, the binder phase may be of the dry or liquid type, but the present invention utilizes a liquid binder system. Liquid binder systems that comprise natural oils, esters and emollients, provide lubricity, cushion and film forming ability. Both natural oils and emollients are excellent pigment dispersants that provide great slip, spreading ability, and improved wear. Some oils enhance skin adhesion, and others help to provide a silky-to-powdery feel. Overall, a liquid binder system improves powder compressibility while reducing dustiness, increases shine of the finished product, and provides a silky-smooth finish on the skin. Nevertheless, even with a liquid binder system, pressed powder compositions are often difficult to stabilize. This is especially true when the concentration of large particle pigments is too great. At some critical point, the particulate phase is unable to completely absorb the liquid binder. This limitation on the concentration of large particle pigments limits the degree of optical effect that can be obtained.

In pressed powder applications, synthetic waxes have been tried as stabilizing agents. These include, but are not limited to, polyolefin wax, paraffin wax, microcrystalline wax, montan wax, polyethylene wax, ceresin, and mixtures thereof. Synthetic waxes, however, tend to be dusty, and unable to provide the requisite adhesion to stabilize compositions that comprise relatively high concentrations of large metallic or pearlescent pigments. Additionally, glittery products tend to have little staying power on the skin. To date, satisfactory results have not been achieved, and there remains a need for a stabilizing agent that is effective to stabilize metallic or pearlescent pigments in pressed powder compositions.

OBJECT OF THE INVENTION

A main object of the present invention is to provide a binder for use in powdery cosmetic compositions, especially those that comprise metallic and pearlescent pigments

SUMMARY OF THE INVENTION

Described herein are binder sub-compositions for use in the binder phase of powdery cosmetics, especially pressed powder compositions. The binder sub-composition consists of one or more viscous emollients, one or more non-viscous emollients, one or more triglyceride ester fatty acids, and one or more flower waxes. The binder sub-composition is preferred for use in pressed cosmetic compositions that comprise metallic and pearlescent pigments. The sub-compositions are able to stabilize metallic and pearlescent particles against fallout. Pressed powder compositions according to the present invention, that utilize the binder sub-composition, have a creamy texture, and are suitable for long-wear (flexible, water-resistant, smudge and flake resistant). The compositions provide true color, excellent color payoff and skin conditioning.

DEFINITIONS

"Comprising" and the like, mean that a list of elements may not be limited to those explicitly recited.

"Consists of" and the like means that a list of elements is limited to those explicitly recited.

Except in operating and comparative examples, or where otherwise explicitly indicated, all numbers in this description indicating amounts or ratios of material or conditions of reaction, physical properties of materials and/or use are to be understood as modified by the word "about."

The terms "stable" and "stability" as used herein refer to a composition which, over a period of at least six months, is substantially unaltered in chemical state, physical homogeneity and/or color when the temperature of the composition varies from about 1° C. to about 40° C.

The term, "powder", as used herein, includes fine and coarse powders, flakes, crystalline flakes, platelets, spherical particles, precipitates, and other solid particulate materials.

DETAILED DESCRIPTION

The present invention relates to cosmetic compositions that comprise a particulate phase and a binder phase.

The Particulate Phase

The particulate phase comprises various cosmetically acceptable powder ingredients and pigments, especially one or more pearlescent and/or metallic pigments. In preferred embodiments of the present invention, the particulate phase comprises one or more pearlescents and/or metallic pigments. These pigments will typically have a diameter (or other characteristic size) in the range of about 0.1 μm to about 500 μm.

The Binder Phase

The binder phase comprises a binder sub-composition that consists of one or more viscous emollients, one or more non-viscous emollients, one or more triglyceride ester fatty acids, and one or more flower waxes. The binder phase may also comprise any cosmetically acceptable liquid ingredients that do not interfere with the function of the binder sub-composition.

Viscous and Non-viscous Emollients

The dynamic viscosity of a liquid is a measure of a liquid's resistance to deformation for a given rate of shear. On a macroscopic level, dynamic viscosity is experienced as a resistance to flow. Binder sub-compositions of the invention comprises one or more viscous emollients and one or more non-viscous emollients. Non-viscous emollients are liquids that exhibit little or no resistance flow. We define a non-viscous emollient as having a dynamic viscosity of less than about 100 mPa·s, more preferably less than about 50 mPa·s. For example, octyldodecyl lactate (INCI name) is a highly polar liquid ester characterized by a dynamic viscosity of about 43 mPa·s. Octyldodecyl lactate has proved to be useful in embodiments of the present invention, and is available as Cosmol-13 from Nisshin OilliO group. In contrast, viscous emollients useful in the present invention will have a dynamic viscosity between about 500 mPa·s and 1000 mPa·s. For example, tridecyl trimellitate (INCI name) is a liquid emollient ester having a dynamic viscosity of about 860 mPa·s. Tridecyl trimellitate is available as Liponate™ TDTM from Vantage Specialty Ingredients (NJ).

Triglyceride Ester Fatty Acid

The binder sub-composition comprises one or more C18-C36 triglyceride ester fatty acids. A triglyceride ester fatty acid is an ester derived from glycerol and three fatty acids. In compositions of the present invention, triglyceride ester fatty acids function to soften waxes and reduce crystallinity. In some embodiments of the present invention, tribehenin (a triglyceride of behenic (C22) acid) is preferred. Tribehenin is available, for example, as Syncrowax™ HRC from Croda, in the form of a non-crystalline paste with a melting point between about 60° C. and 65° C.

Flower Wax

Flower waxes are solid, aromatic plant waxes that are obtained during the production of floral concretes and absolutes. Flower waxes are comprised of the natural wax and aromatics present within the botanical from which they are derived. Flower waxes include, but are not limited to, lavender (*Lavandula angustifolia*), blackcurrant, blue lotus, cassie (*Acacia dealbata*), chamomile, clary sage, everlasting (*Helichrysum angustifolium*), geranium, jasmine, mimosa, nutmeg, orange, rose, tuberose, violet, and mixtures thereof. Preferred flower waxes comprise a mixture of C4-C50 hydrocarbons, which have a characteristic melting point range of about 30° C. to 60° C. (86° F.-140° F.). Longer chain length waxes tend to be too hard for the present invention.

Optional Ingredients

Pressed powder cosmetic compositions of the invention may optionally comprise various cosmetically acceptable ingredients for known beauty or skincare benefits, with the proviso that the ingredients are compatible with the pressed powder product form. Optional ingredients may be in the particulate phase, the binder phase, or both. In practice, any non-particulate ingredients (i.e. liquid, paste) must be added to the liquid binder phase. When present, the total of all optional ingredients will range from about 0.1 to about 20% by weight of the total pressed powder cosmetic composition. Preferred embodiments of the invention comprise no talc, and no silicone.

Optional ingredients include, but are not limited to, antioxidants, preservatives, fragrances, vitamins, antiaging agents, antiwrinkle agents, anti-inflammatories, analgesics, anesthetics, anti-acne agents, antimicrobials, anti-bacterials, anti-yeast agents, antifungal agents, antiviral agents, anti-dandruff agents, anti-dermatitis agents, antipruritic agents, antiemetics, anti-hyperkeratolytic agents, anti-allergenics, antiseptics, anti-dry skin agents, anti-psoriatic agents, anti-seborrheic agents, anti-asthmatic agents, sunscreen agents, antihistamine agents, depigmenting agents, wound-healing agents, corticosteroids, tanning agents, humectants, lubricants, masking agents, medicaments, moisturizers, pH adjusters, chelating agents, emulsifiers, surfactants, thickeners and hormones.

EXAMPLES

The Control Standard for Comparison

In the examples that follow, test samples were prepared according to the pressed powder eyeshadow formula shown in Table 1.

TABLE 1

| Eyeshadow | |
| --- | --- |
| Ingredient | % |
| [1]SP-10 | 2 |
| Aloe vera | 2 |
| [2]Ganzpearl ® GM-0600W | 4.8 |
| [3]Barlux MG (slip modifier) | 5.7 |
| Marshmallow powder | 0.5 |
| [4]Colorona ® chameleon | 44.1 |
| [5]Reflecks ™ Multidimensions transforming teal G780D | 15.2 |
| Binder Phase | 25.0 |
| [6]BarGuard ™ CP/Jeecide Cap-2 (preservatives) | 0.5 |
| [7]Applecare PDS-300 ™ (particle dispersing system) | 0.2 |

[1]Nylon-12 microspheres (Kobo Products, Inc.).
[2]100% polymethyl methacrylate spherical powder.
[3]100% magnesium myristate.
[4]40.0-50.0% mica substrate, 50.0-60.0% iron oxide coating, (EMD Performance Materials); 10-60 μm.
[5]calcium sodium borosilicate/silica/titanium dioxide (CI 77891)/tin oxide (BASF); 27-128 μm.
[6]caprylyl glycol/phenoxyethanol/hexylene glycol (Hampford Research).
[7]caprylic/capric triglyceride/polyhydroxystearic acid/isostearic acid/lecithin/polyglyceryl-3 polyricinoleate (Applechem, Inc.).

A typical traditional binder phase is shown in Table 2.

TABLE 2

| Traditional binder phase | |
| --- | --- |
| Ingredient | % |
| Ceraphyl 375 | 39.9 |
| Cerapyl 847 | 60.0 |
| Vitamin E | 0.1 |

However, when this binder phase is incorporated into the eyeshadow of Table 1, the binder is not absorbed by the powdery ingredients, and at the time of pressing in a pan, liquid seeps from the corners of the pan. The resulting cake is too hard, has chipped corners, exhibits glazing and poor color pay-off. Clearly, a different kind of binder is needed.

The four essential ingredients that make up a binder sub-composition according to the present invention are shown in Table 3. Table 3 shows the relative percentages of one binder sub-composition that gave excellent results, performing well in terms of pressability, stability, drop test, overall appearance, texture and color payoff. An eyeshadow according the formula shown in Table 1, with the binder phase shown in Table 3, constitutes the Standard (control) for comparing variations of the binder sub-composition. Included in the binder phase are two optional liquid ingredients.

TABLE 3

Binder Phase of present invention (standard for testing)

|  | Ingredient | as % of binder phase | as % of Table 1 formula |
|---|---|---|---|
| Binder sub-composition | Tridecyl trimellitate (viscous emollient) | 80.16 | 20.04 |
|  | Octyldodecyl lactate (non-viscous emollient) | 5.34 | 1.35 |
|  | [1]Syncrowax ™ HR-C (triglyceride ester fatty acid) | 2.5 | 0.63 |
|  | Lavender wax (*Lavandula angustifolia*) | 4 | 1 |
| Optional | [2]Dermaxyl | 4 | 1 |
|  | Vitamin E | 4 | 1 |

[1]behenic acid, 1,2,3-propanetriyl ester (Croda, Inc.)
[2]C12-15 Alkyl Benzoate/Tribehenin/Ceramide 2/PEG-10 Phytosterol/Palmitoyl Hexapeptide-12 (Sederma)

EXAMPLES

In the following examples, only the binder phases are shown, the full formula being understood from Table 1. The only difference between the individual test samples is in the concentrations of the ingredients that make up the binder sub-composition shown in Table 3. The concentration of each ingredient is shown as a percentage of the binder phase. One quarter of that amount is the concentration as a percent of the full formula shown in Table 1. Drop test data was collected by dropping a pan of pressed powder from a height of 9 to 15 inches onto a designated surface until breakage.

Example 1

Pressed powders were prepared with the binder phase shown in Table 4, by varying the levels of tridecyl trimellitate, and q.s. to octyldodecyl lactate, while holding all else constant. All trial powders were pressed using the same equipment.

TABLE 4

| Ingredient | Trial 1 | Trial 2 | Trial 3 | Trial 4 |
|---|---|---|---|---|
| Tridecyl trimellitate | 50.0 | 60.0 | 70.0 | 85.0 |
| Octyldodecyl lactate | 35.5 | 25.5 | 15.5 | 0.5 |
| Syncrowax ™ HR-C | 2.5 | 2.5 | 2.5 | 2.5 |
| Lavender wax | 4.0 | 4.0 | 4.0 | 4.0 |
| Dermaxyl | 4.0 | 4.0 | 4.0 | 4.0 |
| Vitamin E | 4.0 | 4.0 | 4.0 | 4.0 |
| Pressing (psi) | 200 | 200 | 200 | 200 |
| Drop test | — | 4 | 10 | 8 |

TABLE 4-continued

| Ingredient | Trial 1 | Trial 2 | Trial 3 | Trial 4 |
|---|---|---|---|---|
| Physical characteristics of cake | composition separates (not stable). Could not press | corners of cake are irregular | less oily than trial 2 | creamy texture |
| Performance |  | slippery, oily feel | more color payoff than trial 2; overall acceptable | powdery feel; intense color payoff; overall comparable to control |

Example 2

Pressed powders were prepared with the binder phase shown in Table 5, by varying the levels of tridecyl trimellitate, and q.s. evenly to other ingredients (except Dermaxyl, whose usage is limited).

TABLE 5

| Ingredient | Trial 5 | Trial 6 | Trial 7 | Trial 8 |
|---|---|---|---|---|
| Tridecyl trimellitate | 50.0 | 60.0 | 70.0 | 85.0 |
| Octyldodecyl lactate | 15.5 | 12.14 | 8.76 | 3.71 |
| Syncrowax ™ HR-C | 7.26 | 5.68 | 4.10 | 1.74 |
| Lavender wax | 11.62 | 9.09 | 6.57 | 2.78 |
| Dermaxyl | 4.0 | 4.0 | 4.0 | 4.0 |
| Vitamin E | 11.62 | 9.09 | 6.57 | 2.78 |
| Pressing (psi) | 200 | 200 | 200 | 200 |
| Drop test | 6 | 22 | 10 | 4 |
| Physical characteristics of cake | harder than control; chips on corners | harder than control; chips on corners | creamy texture; chips on corners | creamy texture; chips on corners |
| Performance | oily feel | oily feel | powdery feel | powdery feel |

Observations from Examples 1 and 2:

Higher levels of tridecyl trimellitate lead to increased color payoff and more creamy, powdery texture. This occurs whether the percentage of octyldodecyl lactate is held constant or varied in proportion to tridecyl trimellitate. We conclude that in some preferred embodiments of the present invention, the binder phase will comprise one or more viscous emollients totaling about 70% to about 85% by total weight of the binder phase (or about 17.5% to about 21.25% by weight of the total powder cosmetic composition).

Example 3

Pressed powders were prepared with the binder phase shown in Table 6 by varying the levels of octyldodecyl lactate, and q.s. to tridecyl trimellitate, while holding all else constant.

TABLE 6

| Ingredient | Trial 1 | Trial 2 | Trial 3 | Trial 4 | Trial 5 | Trial 6 | Trial 7 |
|---|---|---|---|---|---|---|---|
| Tridecyl trimellitate | 85.5 | 84.5 | 83.5 | 82.5 | 81.5 | 80.5 | 75.5 |
| Octyldodecyl lactate | 0 | 1 | 2 | 3 | 4 | 5 | 10 |
| Syncrowax ™ HR-C | 2.5 | 2.5 | 2.5 | 2.5 | 2.5 | 2.5 | 2.5 |
| Lavender wax | 4 | 4 | 4 | 4 | 4 | 4 | 4 |
| Dermaxyl | 4 | 4 | 4 | 4 | 4 | 4 | 4 |
| Vitamin E | 4 | 4 | 4 | 4 | 4 | 4 | 4 |
| Pressing (psi) | 250 | 250 | 250 | 250 | 250 | 250 | 250 |
| Drop test | 19 | 12 | 6 | 11 | 9 | 15 | 11 |
| Physical characteristics of cake | dark tone; no sparkles on surface | dark tone | dark tone | dark tone | dark tone | comparable to standard | comparable to standard |
| Performance | dark color payoff; chunky feel | dark color payoff; chunky feel | dark color payoff; chunky feel | dark color payoff; chunky feel | dark color payoff; chunky feel | | comparable to standard |

| Ingredient | Trial 8 | Trial 9 | Trial 10 | Trial 11 | Trial 12 | Trial 13 | Trial 14 |
|---|---|---|---|---|---|---|---|
| Tridecyl trimellitate | 74.5 | 73.5 | 72.5 | 71.5 | 70.5 | 65.5 | 60.5 |
| Octyldodecyl lactate | 11 | 12 | 13 | 14 | 15 | 20 | 25 |
| Syncrowax ™ HR-C | 2.5 | 2.5 | 2.5 | 2.5 | 2.5 | 2.5 | 2.5 |
| Lavender wax | 4 | 4 | 4 | 4 | 4 | 4 | 4 |
| Dermaxyl | 4 | 4 | 4 | 4 | 4 | 4 | 4 |
| Vitamin E | 4 | 4 | 4 | 4 | 4 | 4 | 4 |
| Pressing (psi) | 250 | 250 | 250 | 250 | 250/150 | 150 | 150 |
| Drop test | 11 | 11 | 11 | 11 | 20/10 | 10 | 10 |
| Physical characteristics of cake | comparable to standard | comparable to standard | comparable to standard | comparable to standard | at 250 psi: glazing; at 150 psi: hard, flaking, no sparkles | hard; breaking on sides; color is off; no sparkles | glazing, hard, flaking |
| Performance | comparable to standard | comparable to standard | comparable to standard | comparable to standard | less color payoff, lighter shade | | |

Observations from Example 3:

When octyldodecyl lactate ranges from about 5%-14% by weight of the binder phase, the results are comparable to the standard. Outside of this range, the results were not acceptable. We conclude that in some preferred embodiments of the present invention, the binder phase will comprise one or more non-viscous emollients totaling about 5% to about 14% by total weight of the binder phase (or about 1.25% to about 3.50% by weight of the total powder cosmetic composition).

Example 4

Pressed powders were prepared with the binder phase shown in Table 7 by varying the levels of triglyceride ester fatty acid (Syncrowax HR-C) and q.s. to tridecyl trimellitate, and holding all else constant.

TABLE 7

| Ingredient | Trial 1 | Trial 2 | Trial 3 | Standard | Trial 4 |
|---|---|---|---|---|---|
| tridecyl trimellitate | 82.66 | 81.66 | 80.66 | 80.16 | 79.66 |
| Octyldodecyl lactate | 5.34 | 5.34 | 5.34 | 5.34 | 5.34 |
| Syncrowax ™ HR-C | 0 | 1 | 2 | 2.5 | 3 |
| Lavender wax | 4 | 4 | 4 | 4 | 4 |
| Dermaxyl | 4 | 4 | 4 | 4 | 4 |
| Vitamin E | 4 | 4 | 4 | 4 | 4 |
| Pressing (psi) | 250 | 250 | 250 | 250 | 250 |
| Drop test | 10 | 9 | 11 | 15 | 8 |

TABLE 7-continued

| | Trial 1 | Trial 2 | Trial 3 | Trial 4 (Standard) | Trial 5 |
|---|---|---|---|---|---|
| Physical characteristics of cake | dark tone; looks frosty; hard; less sparkle on surface | dark tone, looks frosty, less sparkle on surface; accumulation of powder on side of pan | comparable to standard | high metallic finish | dark tone, looks frosty; less sparkle on surface; liquid binder coming through the ribbon |
| Performance | not creamy; poor color payoff | | comparable to standard | creamy, powdery feel; true color; long wear | |

| Ingredient | Trial 5 | Trial 6 | Trial 7 | Trial 8 | Trial 9 |
|---|---|---|---|---|---|
| Tridecyl trimellitate | 78.66 | 77.66 | 72.66 | 67.66 | 62.66 |
| Octyldodecyl lactate | 5.34 | 5.34 | 5.34 | 5.34 | 5.34 |
| Syncrowax ™ HR-C | 4 | 5 | 10 | 15 | 20 |
| Lavender wax | 4 | 4 | 4 | 4 | 4 |
| Dermaxyl | 4 | 4 | 4 | 4 | 4 |
| Vitamin E | 4 | 4 | 4 | 4 | 4 |
| Pressing (psi) | 250 | 250 | 200/150 | 200 | 150 |
| Drop test | 12 | 20+ | 20+/10+ | 20+ | 20+ |
| Physical characteristics of cake | dark tone, looks frosty; less sparkle on surface; liquid binder coming through the ribbon | dark tone, glazing | hard; chips on side | hard; big chips on sides; less sparkle | too hard |
| Performance | | poor color payoff | poor color pay off | poor color pay off | poor color pay off, not lustrous; worst performer |

Observations from Example 4:

We conclude that that in some preferred embodiments of the present invention, the binder phase will comprise one or more triglyceride ester fatty acids totaling about 2.0%-2.5% by total weight of the binder phase (or about 0.50% to about 0.63% by weight of the total powder cosmetic composition). When the concentration of triglyceride ester fatty acids is outside of this range, then the resulting pressed powder compositions are of insufficient quality compared to the standard.

Example 5

Pressed powders were prepared with the binder phase shown in Table 8 by varying the levels of lavender wax and q.s. to tridecyl trimellitate, and holding all else constant.

TABLE 8

| Ingredient | Trial 1 | Trial 2 | Trial 3 | Trial 4 | Standard | Trial 5 | Trial 6 |
|---|---|---|---|---|---|---|---|
| Tridecyl trimellitate | 84.16 | 83.16 | 82.16 | 81.16 | 80.16 | 79.16 | 78.16 |
| Octyldodecyl lactate | 5.34 | 5.34 | 5.34 | 5.34 | 5.34 | 5.34 | 5.34 |
| Syncrowax ™ HR-C | 2.5 | 2.5 | 2.5 | 2.5 | 2.5 | 2.5 | 2.5 |
| Lavender wax | 0 | 1 | 2 | 3 | 4 | 5 | 6 |
| Dermaxyl | 4 | 4 | 4 | 4 | 4 | 4 | 4 |
| Vitamin E | 4 | 4 | 4 | 4 | 4 | 4 | 4 |
| Pressing (psi) | 250 | 250 | 250 | 250 | 250 | 250 | 250 |
| Drop test | 9 | 8 | 5 | 9 | 15 | 8 | 7 |
| Physical characteristics of cake | crumbly | less sparkle | less sparkle | comparable to standard | high metallic finish | comparable to standard | comparable to standard |

TABLE 8-continued

| Ingredient | Trial 1 | Trial 2 | Trial 3 | Trial 4 | Standard | Trial 5 | Trial 6 |
|---|---|---|---|---|---|---|---|
| Performance | Less creamy; lighter payoff | lighter payoff | lighter payoff | comparable to standard | creamy, powdery feel; true color; long wear | comparable to standard | comparable to standard |

TABLE 8

| Ingredient | Trial 7 | Trial 8 | Trial 9 | Trial 10 | Trial 11 | Trial 12 |
|---|---|---|---|---|---|---|
| Tridecyl trimellitate | 77.16 | 76.16 | 75.16 | 74.16 | 69.16 | 64.16 |
| Octyldodecyl lactate | 5.34 | 5.34 | 5.34 | 5.34 | 5.34 | 5.34 |
| Syncrowax ™ HR-C | 2.5 | 2.5 | 2.5 | 2.5 | 2.5 | 2.5 |
| Lavender wax | 7 | 8 | 9 | 10 | 15 | 20 |
| Dermaxyl | 4 | 4 | 4 | 4 | 4 | 4 |
| Vitamin E | 4 | 4 | 4 | 4 | 4 | 4 |
| Pressing (psi) | 250 | 250 | 250 | 250 | 250 | 250 |
| Drop test | 15+ | 15+ | 12 | 8 | 9 | 9 |
| Physical characteristics of cake | comparable to standard | comparable to standard | comparable to standard | some chipping | some chipping | some chipping |
| Performance | comparable to standard | comparable to standard | comparable to standard | comparable to standard | comparable to standard | comparable to standard |

Observations from Example 5:

Test samples with 10% lavender wax or more experienced chipping when pressed. Test samples with 2% lavender wax or less were unacceptable compared to the Standard. Test samples with 3%-9% lavender wax performed similarly to the Standard. We conclude that in some embodiments of the present invention, preferred amounts of lavender wax range from about 3% to about 9% of the binder phase (or about 0.75% to about 2.25% by weight of the total powder cosmetic composition). Most preferred is about 4% to about 5%, based on the total weight of the binder phase (or about 1% to about 1.25% by weight of the total powder cosmetic composition).

Example 6

We wondered flower waxes other than lavender, which has a melting point of about 35° C., are useful in the binder sub-composition. Pressed powders were prepared with the binder phase shown in Table 9 by replacing lavender wax in the Standard binder phase (Table 3) with various other flower waxes whose melting points range from about 30° C. to 60° C. (86° F.-140° F.) (trials 1-6). A non-floral wax, ozokerite, is included for comparison (trial 7). Ozokerite is a hydrocarbon wax derived from mineral or petroleum sources. We used a microcrystalline wax that melts over a range between 70° C. and 97° C.

TABLE 9

| Ingredient | Trial 1 | Trial 2 | Trial 3 | Trial 4 | Trial 5 | Trial 6 | Trial 7 |
|---|---|---|---|---|---|---|---|
| Tridecyl trimellitate | 80.16 | 80.16 | 80.16 | 80.16 | 80.16 | 80.16 | 80.16 |
| Octyldodecyl lactate | 5.34 | 5.34 | 5.34 | 5.34 | 5.34 | 5.34 | 5.34 |
| Syncrowax ™ HR-C | 2.5 | 2.5 | 2.5 | 2.5 | 2.5 | 2.5 | 2.5 |
| Dermaxyl | 4 | 4 | 4 | 4 | 4 | 4 | 4 |
| Vitamin E | 4 | 4 | 4 | 4 | 4 | 4 | 4 |
| Jasmine wax (*Jasminum Officinale*) (35° C.) | 4 | | | | | | |
| Rose wax (*Rosa Centifolia/ Rosa Damascena*) (35°) | | 4 | | | | | |

TABLE 9-continued

| Ingredient | Trial 1 | Trial 2 | Trial 3 | Trial 4 | Trial 5 | Trial 6 | Trial 7 |
|---|---|---|---|---|---|---|---|
| Jojoba esters (tradename: Floraesters ® 20) (45-60° C.) | | | 4 | | | | |
| Jojoba esters (tradename: Floraspheres ® Jojoba LGS White) (50-60° C.) | | | | 4 | | | |
| Bayberry wax (*Myrica Ceriefera*) (38-46° C.) | | | | | 4 | | |
| Jojoba esters (tradename: Floraesters ® 30) (47-51° C.) | | | | | | 4 | |
| Synthetic Ozokerite (70-90° C.) | | | | | | | 4 |

Observations from Example 6:

Trials 1-6 performed comparably to the Standard with lavender wax. Trial 7 performed unacceptably. The cake was too hard and glazing occurred. The corners chipped when pressing. We conclude that in some preferred embodiments of the present invention, the binder phase will comprise one or more C4-C50 hydrocarbon flower waxes that have melting point ranges between 30° C. and 60° C.

Example 7

In this Example, we removed all waxy ingredients from the Standard binder sub-composition (Table 3) and q.s. tridecyl trimellitate.

TABLE 10

| Ingredient | Trial 1 |
|---|---|
| Tridecyl trimellitate (viscous emollient) | 86.66 |
| Octyldodecyl lactate (non-viscous emollient) | 5.34 |
| [1]Dermaxyl | 4 |
| Vitamin E | 4 |

[1]C12-15 Alkyl Benzoate/Tribehenin/Ceramide 2/PEG-10 Phytosterol/Palmitoyl Hexapeptide-12 (Sederma)

Observations from Example 7:

Incorporating the binder phase of table 10 into the base formula (table 1) resulted in an unacceptable, dusty, crumbly cake.

Example 8

Table 11 shows the results when tridecyl trimellitate (viscosity=859.4 mPa·s) is replaced with emollients of varying viscosities.

TABLE 11

| Ingredient | Trial 1 | Trial 2 | Trial 3 | Trial 4 |
|---|---|---|---|---|
| [1]Cetiol ® LC (9-12 mPa · s) | 80.16 | | | |
| [2]Cosmol ™ 43V (448 mPa · s) | | 80.16 | | |
| [3]Dermol ™ L45 (900 mPa · s) | | | 80.16 | |
| [4]CosmoSurf ® M (83,000 mPa · s) | | | | 80.16 |
| Octyldodecyl lactate | 5.34 | 5.34 | 5.34 | 5.34 |
| Syncrowax ™ HR-C | 2.5 | 2.5 | 2.5 | 2.5 |
| Lavender wax | 7 | 8 | 8 | 9 |
| Dermaxyl | 4 | 4 | 4 | 4 |
| Vitamin E | 4 | 4 | 4 | 4 |
| Pressing (psi) | 250/150 | 150 | 150 | 150 |
| Drop test | — | 9 | 15+ | 20+ |
| Physical characteristics of cake | liquids from all around when pressed at 150 or 250 psi | accumulation of powder on the sides; harder than standard; glazing. | | Sticky and drier than standard; more sparkly than standard |
| Performance | — | Color and pay-off comparable to standard | Color and pay-off comparable to standard | Crumbles when applied to skin |

[1]Fatty acids, C8-10, C12-18-alkyl esters (INCI name: Coco-Caprylate/Caprate) (BASF)
[2]Diglyceryl triisostearate (INCI name: Polyglyceryl-2 Triisostearate) (Nisshin Oillio Group, Ltd.)
[3]Poly(oxy-1,2-ethanediyl), .alpha., .alpha.', .alpha."-1,2,3-propanetriyltris[.omega.-hydroxy-, 2-hydroxypropanoate (INCI Name: Glycereth-5 Lactate) (ALZO, International)
[4](Surfatech Corp)

Observations from Example 8:

When tridecyl trimellitate (viscosity=859.4 mPa·s) was replaced with an emollient whose dynamic viscosity is orders of magnitude higher or lower, then the resulting binder sub-composition does not perform well. In contrast, the performance of Cosmol™ 43V (448 mPa·s) was comparable to the control, in some aspects, and the performance of Dermol™ L45 (900 mPa·s) was even better. We conclude that in some preferred embodiments of the present invention, the viscous emollient component of the binder sub-composition should have a dynamic viscosity between about 500 mPa·s and 1000 mPa·s.

Example 9

The present invention relates to compositions for application to a skin surface. We have discussed the benefits of our binder sub-composition in terms of a pressed powder eyeshadow. However, the binder sub-composition according to the present invention may find uses in various other cosmetic products. For example, a blush composition that utilizes the standard binder sub-composition was formed by pressing at 300 psi. Aesthetics were acceptable, and the blush accomplished four drops in the drop test. A face powder composition that utilizes the standard binder sub-composition was formed by pressing at 400 psi. Aesthetics were acceptable, and the face powder survived two drops in the drop test. Overall, the binder formula can be pressed in different pan sizes, adjusting the pressure to ensure that the pressed formula passes a drop test without compromising the aesthetics of the product. In contrast to a pressed powder form, a loose powder composition was made by decreasing the binder phase from 25% to about 7% of the total loose powder composition, with q.s. to pearl particles. The aesthetics were acceptable. Our observations lead us to conclude that a binder phase according to the present invention is useful in powder cosmetics at concentrations that range from about 7% to about 25% of the total powder cosmetic composition.

Example 10

In the particulate phase, the concentration of a relatively larger pearlescent pigment (Glassmira OM24) was increased, and q.s. to a relatively smaller pearlescent pigment (Syncrystal Almond). All else was held constant.

TABLE 12

| Ingredient | Trial 1 | Trial 2 | Trial 3 | Trial 4 |
|---|---|---|---|---|
| [1]SP-10 | 2 | 2 | 2 | 2 |
| Aloe vera | 2 | 2 | 2 | 2 |
| [2]Ganzpearl ® GM-0600W | 4.8 | 4.8 | 4.8 | 4.8 |
| [3]Barlux MG | 5.7 | 5.7 | 5.7 | 5.7 |
| Marshmallow powder | 0.5 | 0.5 | 0.5 | 0.5 |
| [4]Syncrystal Almond | 44.2 | 39.2 | 34.2 | 44.2 |
| [5]Glassmira OM24 | 15.2 | 20.2 | 25.2 | 15.2 |
| [6]BarGuard ™ CP/Jeecide Cap-2 (preservatives) | 0.5 | 0.5 | 0.5 | 0.5 |
| Binder phase of Table 3 (present invention) | 25 | 25 | 25 | — |
| Binder phase of Table 2 (traditional) | — | — | — | 25 |
| [7]Applecare PDS-300 ™ | 0.1 | 0.1 | 0.1 | 0.1 |
| Pressing (psi) | 200 | 200 | 200 | 250 |
| Drop test | 8 | 9 | 10 | — |
| Physical characteristics of cake | Comparable to standard | Comparable to standard | Flaky mass, but able to press | Not able to press |

[1]Nylon-12 microspheres (Kobo Products, Inc.).
[2]100% polymethyl methacrylate spherical powder.
[3]100% magnesium myristate.
[4]synthetic fluorphlogopite coated with titanium dioxide and iron oxides (free flowing powder) 20-25 μm.
[5]Al · Ca · Na · Silicate, Iron (III) Oxide, Silica (pearlescent pigment 20-500 μm).
[6]caprylyl glycol/phenoxyethanol/hexylene glycol (Hampford Research).
7caprylic/capric triglyceride/polyhydroxystearic acid/isostearic acid/lecithin/polyglyceryl-3 polyricinoleate (Applechem, Inc.).

Observations from Example 10:

In trial 4 (traditional binder phase) the mass could not be pressed into a cake. Liquid overflowed on all sides of the pan, which indicates that the powders were not able to absorb the traditional binder due to the presence of large pearl particles, even at the lowest concentration tested. In contrast, with a binder sub-composition according to the present invention, cakes could be pressed, even when the concentration of large pearl particles was as high as 25.2%, by weight of the total powder cosmetic composition.

We have described powdery cosmetic compositions that comprise a particulate phase and a binder phase. The binder phase comprises a binder sub-composition. The binder sub-composition is particularly suited for use in stabilizing pearlescent and metallic pigments. The compositions are stable, have a creamy texture, and are suitable for long-wear, while providing true color, excellent color payoff and skin conditioning. While particular embodiments of the present invention have been illustrated and described, it would be obvious to those skilled in the art that various other changes and modifications can be made without departing from the spirit and scope of the invention. It is therefore, intended to cover, in the appended claims, all such changes and modifications that are within the scope of this invention.

What is claimed is:

1. A powdery cosmetic composition that comprises a particulate phase and a binder phase, wherein:
   the particulate phase comprises up to 25% by weight of the powdery cosmetic composition of one or more cosmetically acceptable pearlescent and/or metallic pigments
   the binder phase comprises a binder sub-composition that consists of:
      17.5% to 21.25% by weight of the powdery cosmetic composition, of one or more viscous emollients that have a dynamic viscosity between 500 mPa·s and 1000 mPa·s;
      1.25% to 3.5% by weight of the powdery cosmetic composition, of one or more non-viscous emollients that have a dynamic viscosity less than 100 mPa·s;
      0.50% to 0.63% by weight of the powdery cosmetic composition, of one or more C18-C36 triglyceride ester fatty acids;
      0.75% to 2.25% by weight of the powdery cosmetic composition, of one or more C4-C50 hydrocarbon flower waxes that have melting point ranges between 30° C. and 60° C.

2. The powdery cosmetic composition according to claim 1 wherein the particulate phase comprises one or more types of particulate materials characterized by a size of 0.1 μm to 500 μm.

3. The powdery cosmetic composition of claim 2, wherein the cosmetic composition is a pressed powder cosmetic.

4. The powdery cosmetic composition according to claim 1 wherein the one or more viscous emollients is tridecyl trimellitate.

5. The powdery cosmetic composition according to claim 1 wherein the one or more non-viscous emollients is octyldodecyl lactate.

6. The powdery cosmetic composition according to claim 1 wherein the one or more C18-C36 triglyceride ester fatty acids is tribehenin.

7. The powdery cosmetic composition according to claim 1 wherein the one or more C4-C50 hydrocarbon flower waxes is lavender wax.

8. The powdery cosmetic composition of claim 1 that further comprises 0.1% to 20% by weight of the powdery cosmetic composition, of one or more cosmetically acceptable ingredients.

\* \* \* \* \*